(12) United States Patent
Kahmer

(10) Patent No.: US 11,730,493 B2
(45) Date of Patent: Aug. 22, 2023

(54) METHODS AND APPARATUS FOR PERFORMING DISCECTOMY

(71) Applicant: GLOBUS MEDICAL, INC., Audubon, PA (US)

(72) Inventor: Damien Kahmer, Glenside, PA (US)

(73) Assignee: Globus Medical Inc., Audubon, PA (US)

(*) Notice: Subject to any disclaimer, the term of this patent is extended or adjusted under 35 U.S.C. 154(b) by 0 days.

(21) Appl. No.: 17/586,019

(22) Filed: Jan. 27, 2022

(65) Prior Publication Data

US 2022/0218363 A1 Jul. 14, 2022

Related U.S. Application Data

(63) Continuation of application No. 16/282,656, filed on Feb. 22, 2019, now Pat. No. 11,234,716.

(51) Int. Cl.
*A61B 17/16* (2006.01)
*A61B 17/00* (2006.01)
*A61B 90/00* (2016.01)

(52) U.S. Cl.
CPC .. *A61B 17/1671* (2013.01); *A61B 2017/0046* (2013.01); *A61B 2017/00261* (2013.01); *A61B 2017/00367* (2013.01); *A61B 2090/0811* (2016.02)

(58) Field of Classification Search
CPC ........ A61B 17/1671; A61B 2090/0811; A61B 2017/00261; A61B 2017/00367; A61B 2017/0046; B26B 1/02; B26B 1/048; B26B 1/08; B26B 1/046; B26B 5/001

USPC .......................................... 30/154, 155, 162
See application file for complete search history.

(56) References Cited

U.S. PATENT DOCUMENTS

| | | | |
|---|---|---|---|
| 3,186,026 A | 6/1965 | Serio | |
| 3,430,345 A | 3/1969 | Abreu | |
| 5,308,358 A * | 5/1994 | Bond | A61B 17/29 606/174 |
| 5,649,947 A | 7/1997 | Auerbach et al. | |
| 5,836,958 A | 11/1998 | Ralph | |
| 5,916,230 A | 6/1999 | Brenneman et al. | |
| 5,928,239 A | 7/1999 | Mirza | |
| 6,358,251 B1 | 3/2002 | Mirza | |
| 6,383,188 B2 | 5/2002 | Kuslich et al. | |
| 6,575,978 B2 * | 6/2003 | Peterson | A61B 17/1604 606/171 |
| 6,645,219 B2 | 11/2003 | Roe | |
| 6,923,813 B2 | 8/2005 | Phillips et al. | |
| 8,652,139 B2 | 2/2014 | Sterrett et al. | |
| 8,852,190 B2 | 10/2014 | Sherman | |

(Continued)

FOREIGN PATENT DOCUMENTS

| DE | 102016212300 A1 | 1/2018 |
|---|---|---|
| WO | 2018007045 A1 | 1/2018 |

*Primary Examiner* — Kevin T Truong
*Assistant Examiner* — Tracy L Kamikawa

(57) ABSTRACT

Methods and apparatus for performing a discectomy are disclosed herein. In some embodiments, a surgical tool for use in a therapeutic treatment of a patient includes a handle; an upper arm coupled to the handle; a lower arm coupled to the handle; a pivot arm coupled to one of the upper arm or the lower arm via a first pivot pin; and an end effector pivotably coupled to the pivot arm via a second pivot pin, wherein actuation of the handle causes movement of the pivot arm and articulation of the end effector.

18 Claims, 16 Drawing Sheets

(56) References Cited

U.S. PATENT DOCUMENTS

| | | |
|---|---|---|
| 9,226,764 B2 | 1/2016 | O'Neil et al. |
| 9,585,650 B2 * | 3/2017 | Lim ................... A61B 17/025 |
| 9,750,499 B2 | 9/2017 | Leimbach et al. |
| 2007/0123889 A1 | 5/2007 | Malandain et al. |
| 2008/0077241 A1 * | 3/2008 | Nguyen ................ A61F 2/4684 |
| | | 606/85 |
| 2012/0271313 A1 | 10/2012 | Lauchner |
| 2013/0325048 A1 * | 12/2013 | Weiman ............... A61B 17/025 |
| | | 606/1 |

* cited by examiner

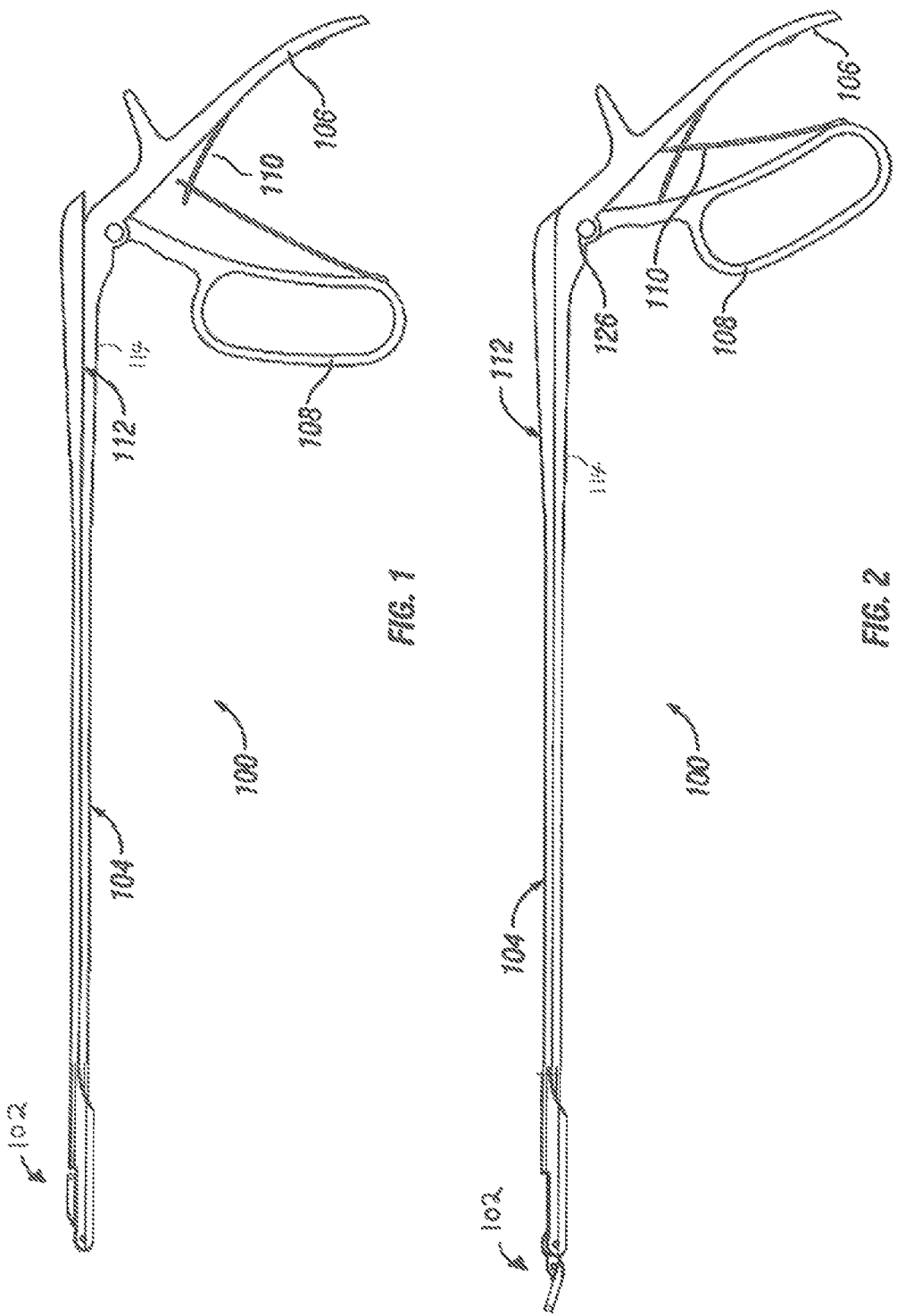

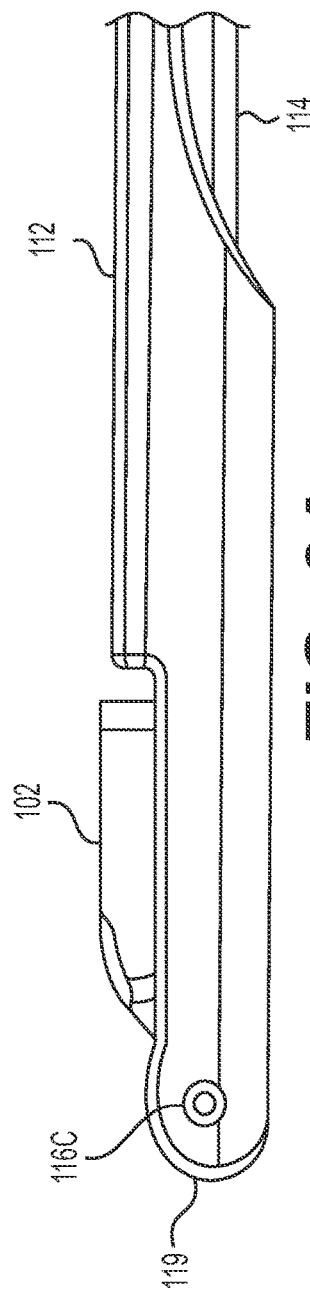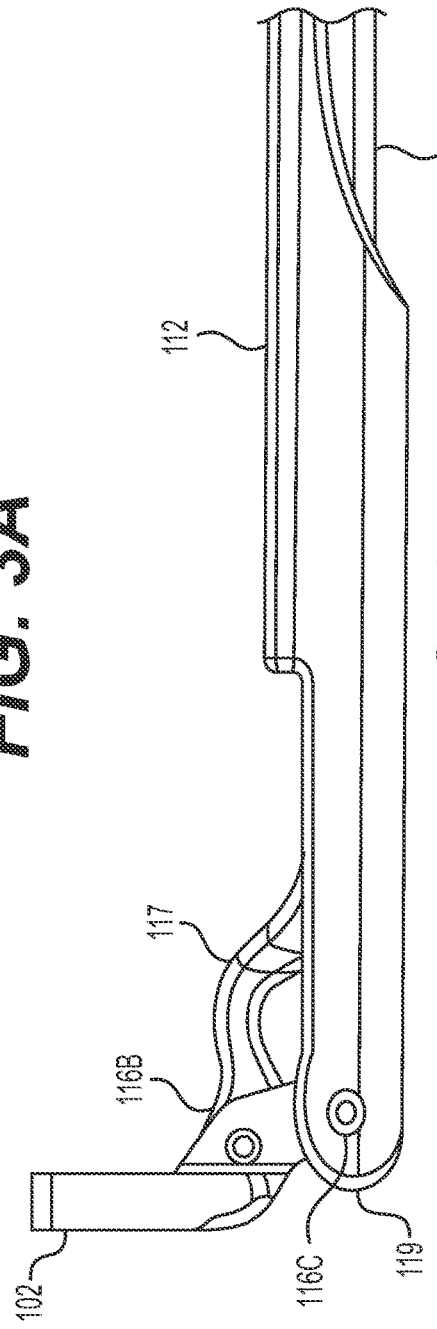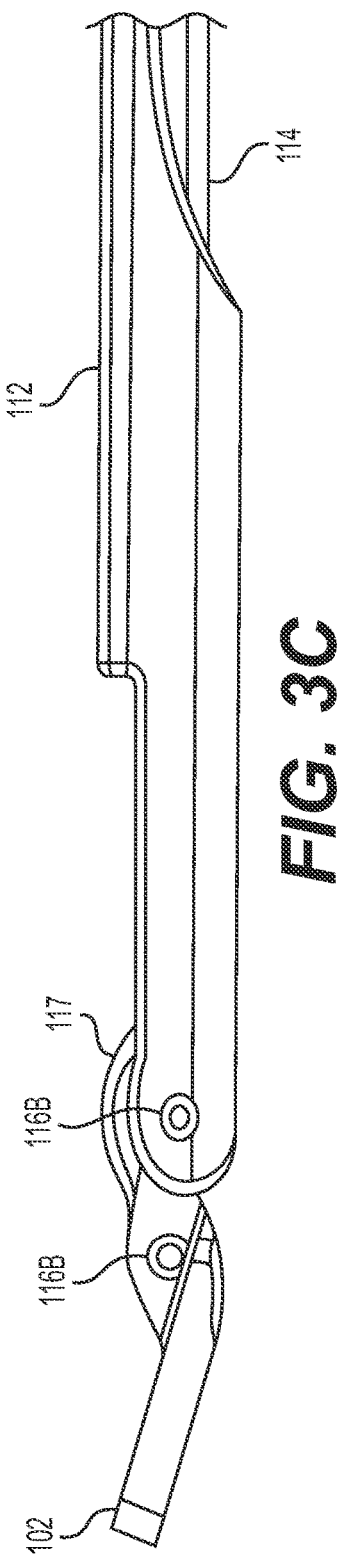

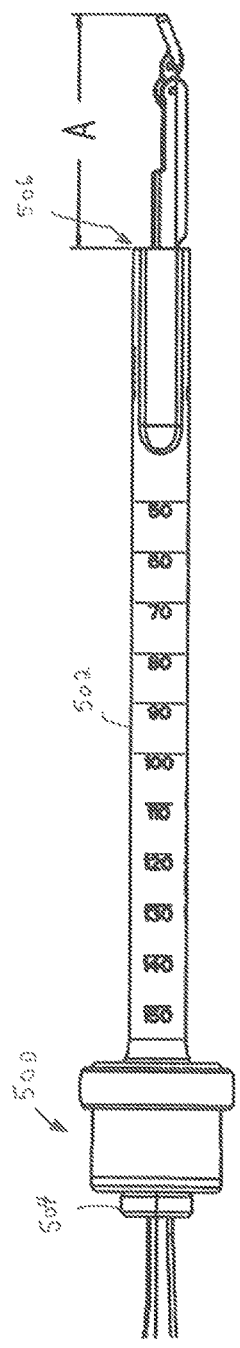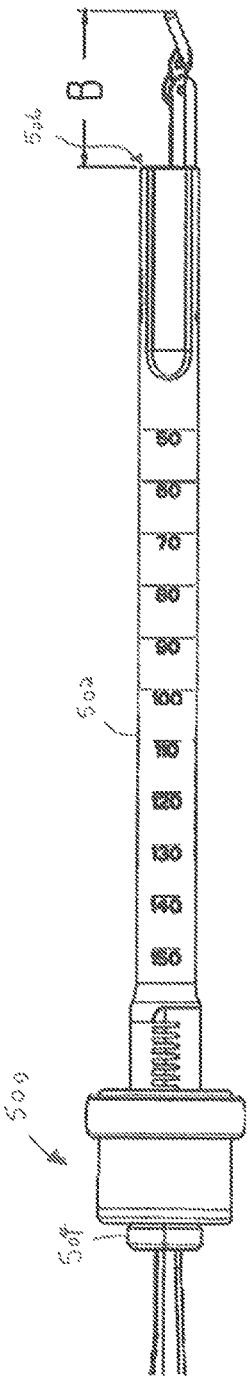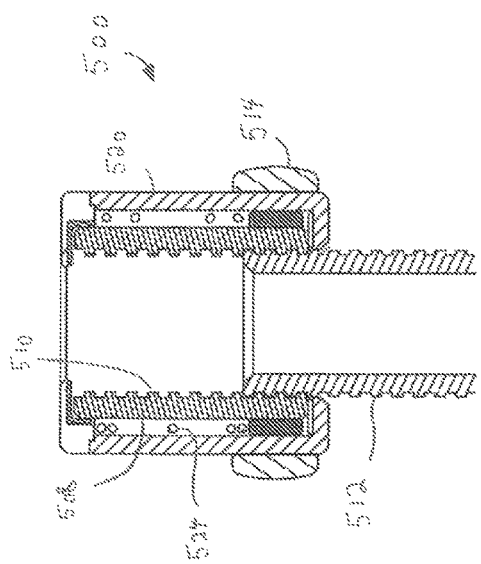

METHODS AND APPARATUS FOR
PERFORMING DISCECTOMY

CROSS-REFERENCE TO RELATED APPLICATIONS

The present application is a continuation of U.S. patent application Ser. No. 16/282,656, filed on Feb. 22, 2019, now U.S. Pat. No. 11,234,716, which is incorporated herein in its entirety.

FIELD OF THE INVENTION

The invention relates to methods and apparatus for performing a discectomy.

BACKGROUND OF THE INVENTION

Bones and bony structures are susceptible to a variety of weaknesses that can affect their ability to provide support and structure. Weaknesses in bony structures have numerous potential causes, including degenerative diseases, tumors, fractures, and dislocations. Advances in medicine and engineering have provided doctors with a plurality of devices and techniques for alleviating or curing these weaknesses.

In some cases, the spinal column requires additional support in order to address such weaknesses. One technique for providing support is to extend a structure between adjacent bones, the structure connected at each end to a polyaxial screw "tulip", or yoke, connected to a bone screw inserted within the bone.

Preparation of the intervertebral disc space includes maneuvering a cutting tool within a small space. Access to the disc space may be limited, as well, for example when conducting a minimally invasive procedure. The foregoing and other diseases often require the removal or shaping of body tissue through a minimal incision, for example in a laparoscopic procedure, where the tool must be sufficiently small to pass through a small opening in the body.

It is desirable to separate the nucleus from the annulus within the intervertebral disc space while also bring able to fit the disc prep tool through a small diameter cannula extending through the incision. Removal of tissue from the endplates of the vertebrae adjacent the disc space can be accomplished with various instruments. However, it is difficult to cut vertically through the disc so as to separate the degenerated nucleus from the annular tissue. It is also necessary to ensure that the annulus furthest away from the incision (e.g., contralateral in a lateral procedure) is not cut. It is also necessary to address the varying levels of curvature that different patients have when removing cartilaginous tissue from the endplates.

SUMMARY OF THE INVENTION

Embodiments of methods and apparatus for performing a discectomy are disclosed herein. In some embodiments, a surgical tool for use in a therapeutic treatment of a patient includes a handle; an upper arm coupled to the handle; a lower arm coupled to the handle; a pivot arm coupled to one of the upper arm or the lower arm via a first pivot pin; and an end effector pivotably coupled to the pivot arm via a second pivot pin, wherein actuation of the handle causes movement of the pivot arm and articulation of the end effector.

In some embodiments, a surgical tool for use in a therapeutic treatment of a patient, includes a handle extending from a proximal end to a distal end. an upper arm coupled to the handle; a lower arm coupled to the handle; a pivot arm coupled to one of the upper arm or the lower arm via a first pivot pin; and an end effector pivotably coupled to the pivot arm via a second pivot pin, wherein actuation of the handle causes movement of the pivot arm and articulation of the end effector. The handle includes a body having a central channel extending from a distal end to a point between the proximal end and the distal end; a carrier disposed around the body and having external threads; a knob surrounding the body and carrier, the knob having internal threads corresponding to the external threads of the carrier, wherein rotation of the knob causes linear translation of the carrier along an axis of the handle; an attachment arm disposed within the central channel and coupled to the carrier via a pin, wherein the attachment arm configured to mate with a corresponding feature of the surgical tool.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 1 depicts a discectomy instrument in a retracted position in accordance with embodiments of the present disclosure;

FIG. 2 depicts the discectomy instrument of FIG. 1 in an extended position;

FIGS. 3A-3C depict an articulating end of a discectomy tool in accordance with embodiments of the present disclosure;

FIGS. 5A-5E depict an adjustable stop for use with a discectomy tool in accordance with embodiments of the present disclosure;

DETAILED DESCRIPTION OF THE INVENTION

Figure 4A:
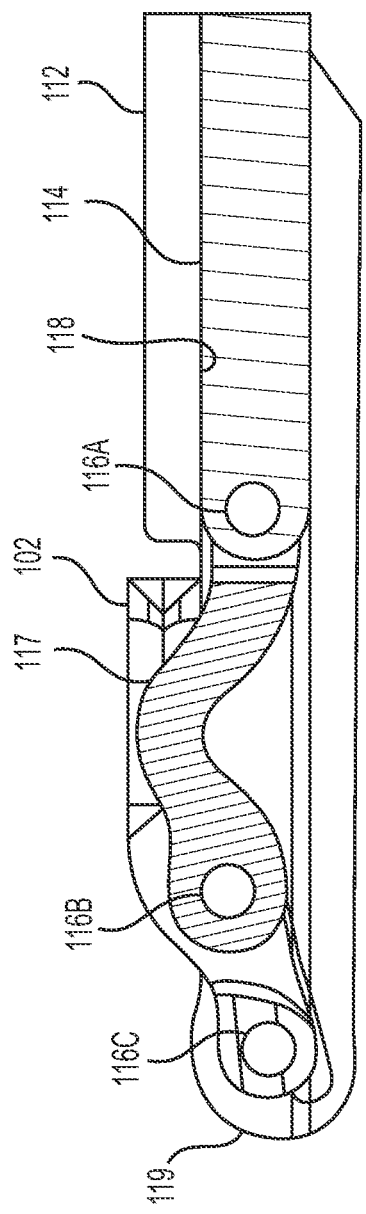
FIGS. 4A-4B depict cross-sectional views of the articulating end effector of a discectomy tool in accordance with embodiments of the present disclosure.

With reference to FIGS. 1 and 2, a surgical instrument, or tool 100 in accordance with some embodiments of the present disclosure will be described. In some embodiments, the tool 100 includes an articulating end effector 102, in this embodiment a ring curette for cutting tissue. For example, tool 100 may be used to prepare vertebral endplates, or an intervertebral space, for insertion of a stabilizing implant. Tool 100 enables a large angle of articulation of end effector 102, which can have various shapes, as will be discussed below. Moreover, tool 100 may be used to articulate one or more of any type of device, including but not limited to the examples of cutter, curette, pincher, grasper, light source, dilator, clamp, hose, retractor, sensor, other articulating tool, or optical device. Tool 100 further advantageously includes an extension 104, a handle 106 connected to extension 104, a moveable trigger 108, and a trigger bias 110 operative to return trigger 108 to a starting position after actuation.

While a surgical instrument particularly benefits from the disclosure, it should be understood that any tool requiring a wide range of motion, insertable through a small opening, may be fabricated in accordance with the disclosure. This may include, for example, mechanical repair or assembly tools.

Extension 104 includes an upper arm 112 and a lower arm 114 which are mutually connected whereby lower arm 114 is affixed to handle 106, and upper arm 112 is caused to slide relative to lower arm 114 as trigger 108 is actuated or operated. Lower arm 114 and upper arm 112 may be connected by any known means, including a dovetail or other mutually interlocking configuration, or lower arm 114 may form an enclosure or sleeve containing upper arm 112.

In accordance with the disclosure, upper arm 112 and lower arm 114 are elongated and narrow, such that they may form a laparoscopic instrument passable into the body of a patient through a cannula extending through minimally invasive incision, for example though a stab type incision which may be less than 30 mm in length, for example about 15 mm in length, but may be larger as deemed therapeutically best by the medical practitioner. Typically, such instruments form a total width of less than 15 mm, and in most cases substantially less than 15 mm, for example about 6 mm or less. The upper arm 112 extends from a proximal end to a distal end. The distal end of the upper arm includes a channel 118, through which a distal end of the lower arm 114 passes.

Figure 4B:
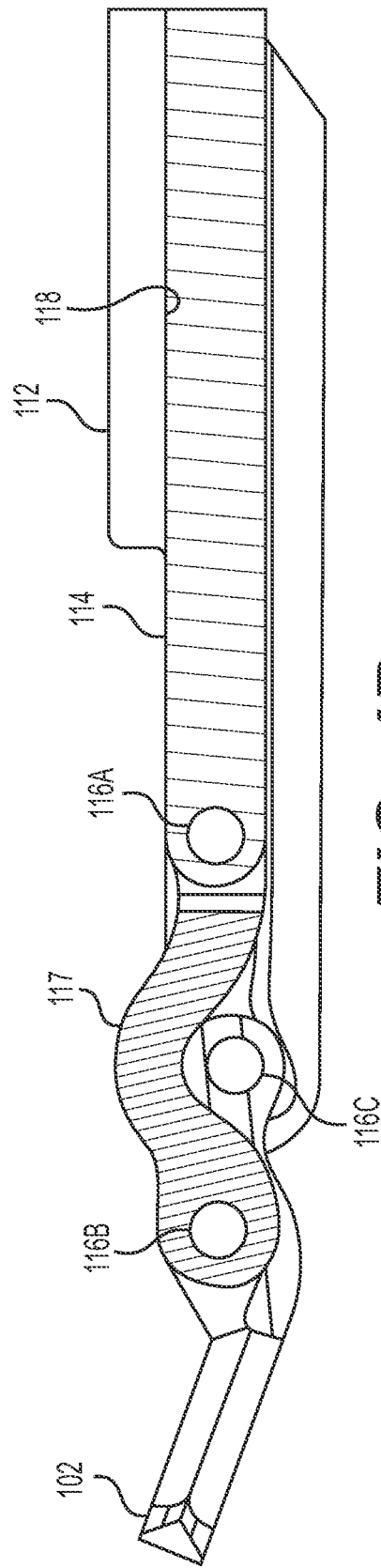

FIGS. 3A-3C depict side views of the tool 100 in an initial position, intermediary position, and fully extended position of the end effector 102, respectively. FIGS. 4A and 4B depict cross-sectional views of the tool 100 in the initial and fully extended positions, respectively. With reference to FIGS. 3A-3C and 4A-4B, end effector 102 operates on an active pivoting mechanism which includes a first pivot pin 116A, a second pivot pin 116B, and a third pivot pin 116C. The first pivot pin 116A is fixed to the distal end of the lower arm 114 and a proximal end of a pivot arm 117. The first pivot pin is configured to translate along the channel 118. The second pivot pin 116B is fixed to the end effector 102 and a distal end of the pivot arm 117, thus allowing the second pivot pin 116B to move about the third pivot pin 116C, as discussed below. The third pivot pin 116C is fixed to a distal tip 119 of the upper arm 112 and to the end effector 102, thus allowing the end effector 102 to rotate about a pivot axis passing through the third pivot pin 116C. As a result, when the trigger 108 is actuated, the lower arm 114 translates relative to the upper arm 112, moving the lower arm 114 forward. This forward movement of the lower arm 114 pushes the second pivot pin 116B beyond the first pivot pin 116A (as shown in FIGS. 3C and 4B) because of the curvature of the pivot arm 117. The movement of the second pivot pin 116B beyond the first pivot pin 116A advantageously provides a sweep angle of about 160°. Such a large sweep advantageously provides an improved ability to separate the nucleus of the disc from the annulus and allows for the insertion of the tool either in the initial position or in the fully extended position. The geometry of the end effector 102 (i.e., the opening in the ring curette) advantageously allows a portion of the pivot arm 117 to be disposed within the end effector 102 in the initial position, thus maintaining a low profile of the tool 100 during insertion.

In some instances, however, great care must be exercised not to cut through the annulus of the disc on the side of the disc space opposite insertion of the tool. In such instances, the surgeon may wish to limit the amount of travel of the end effector of the tool to a predetermined amount of travel. Typically, instruments are marked with length indicators and it is up to the surgeon to determine how far into the disc space the tool has been inserted or how far beyond a distal end of a cannula the tool extends based on these markings. As such, the inventors have developed an adjustable stop 500 configured to limit the amount of travel of the end effector of a surgical tool. The travel allowance can be adjusted within a range defined by the surgeon at the beginning of the surgery. However, the surgeon may also change that travel allowance mid-surgery, if necessary.

Figure 5D:
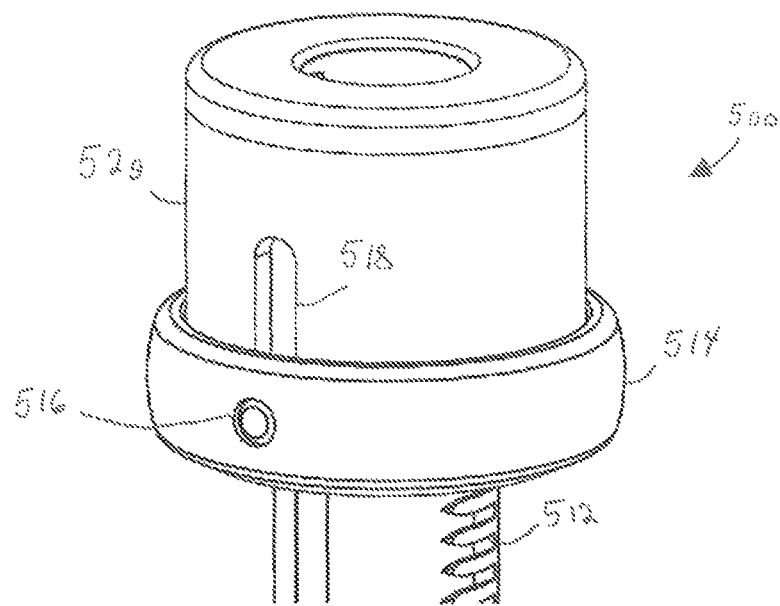

FIGS. 5A-5E depict an adjustable stop 500 for use with a surgical tool (e.g., tool 100 described above) to limit the amount of travel of the end effector of the tool into the disc space. The adjustable stop 500 is coupled to a cannula 502 through which the tool is inserted into the disc space. Each tool includes a hard stop 504 (e.g., a collar or shoulder) that typically limits the amount of travel of the tool through the cannula 502. The adjustable stop 500 is moved to a desired position along the cannula 502 such that when the hard stop 504 contacts the adjustable stop 500, the tool cannot be advanced further into the cannula 502. As a result, the distance traveled by the end effector of the tool beyond a distal end 506 of the cannula 502 is limited to a desired distance. FIG. 5A depicts the adjustable stop 500 positioned at the lowest position along a proximal portion of the cannula 502. The tool protrudes beyond the distal end 506 of the cannula 502 a distance A at this stop position. FIG. 5B depicts the adjustable stop 500 position at the highest setting along the proximal portion of the cannula 502. The tool protrudes beyond the distal end 506 of the cannula a distance B, which is less than the distance A, at this position.

Figure 5E:
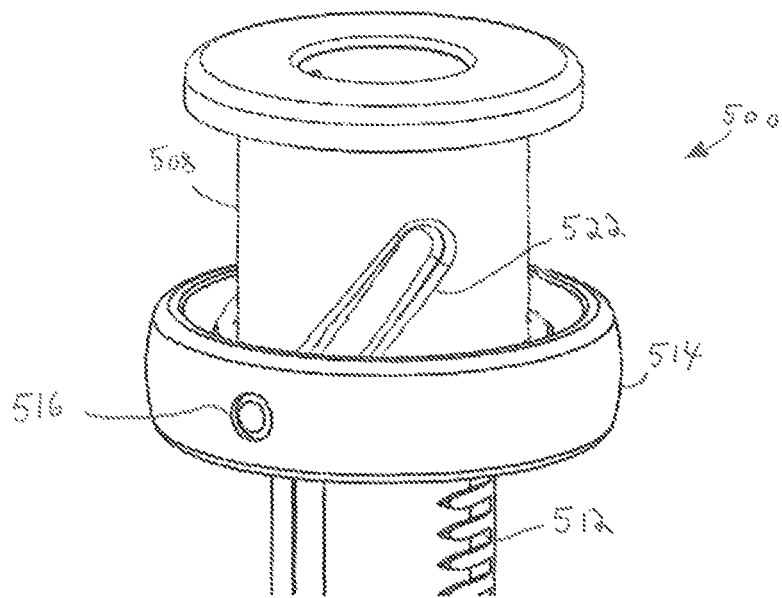

In some embodiments, the position of the adjustable stop 500 is adjustable using interacting features on the proximal portion of the cannula 502. In such an embodiment, the adjustable stop 500 includes an internal body 508 that includes a first set of teeth 510 that mate with a second set of teeth 512 on the cannula 502. When the first and second sets of teeth 510, 512 are engaged, the adjustable stop 500 is prevented from moving along the cannula 502. When the teeth are disengaged, the position of the adjustable stop 500 may be adjusted. To engage and disengage the teeth, the internal body is rotated such that the first set of teeth 510 are rotated out of engagement with the second set of teeth 512. In some embodiments, to rotate the first set of teeth 510 out of engagement, a collar 514 of the adjustable 500 may be pulled back (i.e., proximally). The collar 514 includes a radially inward extending pin 516 that extends through a linear slot 518 formed in an outer housing 520 and a helical slot 522 formed in the internal body 508. FIG. 5D depicts the adjustable stop 500 with the outer housing 520. FIG. 5E depicts the adjustable stop 500 without the outer housing 520. As the collar 514 is pulled back, its motion is constrained by pin 516 in the linear slot 518 and the internal body 508 is caused to rotate due to the motion of the pin 516 along the helical slot 522. As depicted in FIG. 5C, an internal spring 524 is disposed between the outer housing 520 and the internal body 508 to bias the collar 514 distally (i.e., towards a position in which the first and second sets of teeth 510, 512 are in engagement).

Figure 6A:
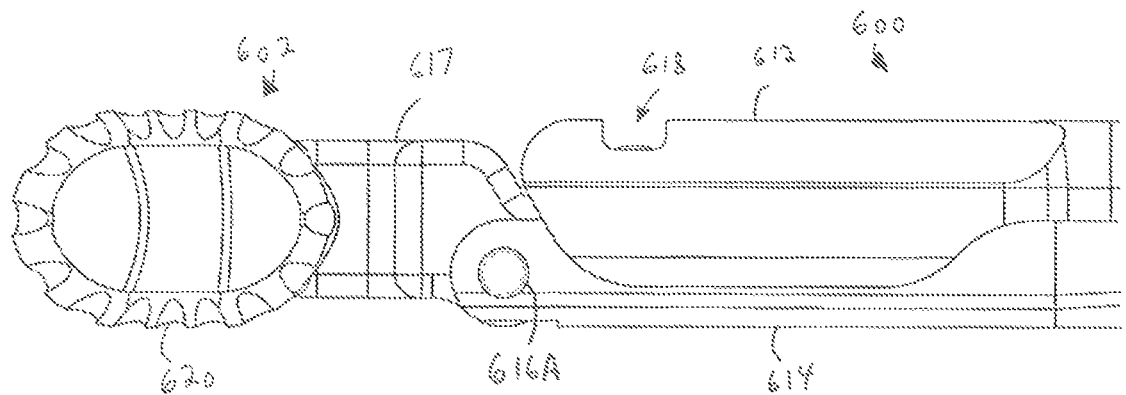
FIGS. 6A-6B depict an articulating end of a discectomy tool in accordance with embodiments of the present disclosure.
Figure 6B:
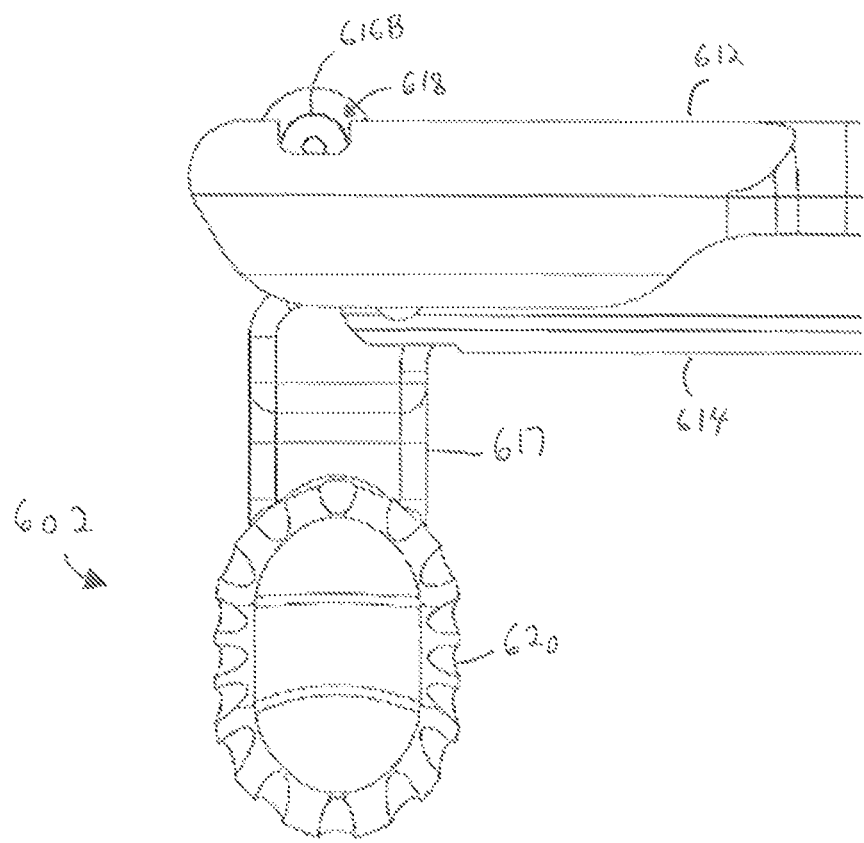
Figure 7A:
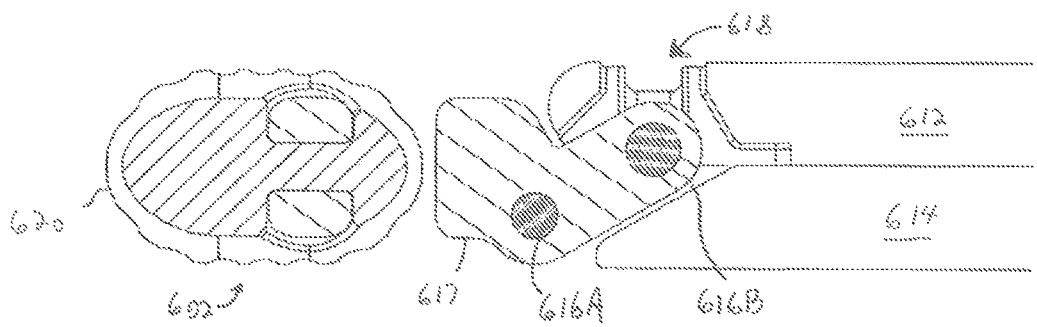
FIGS. 7A-7C depict cross-sectional views of the articulating end effector of a discectomy tool in accordance with embodiments of the present disclosure.
Figure 7B:
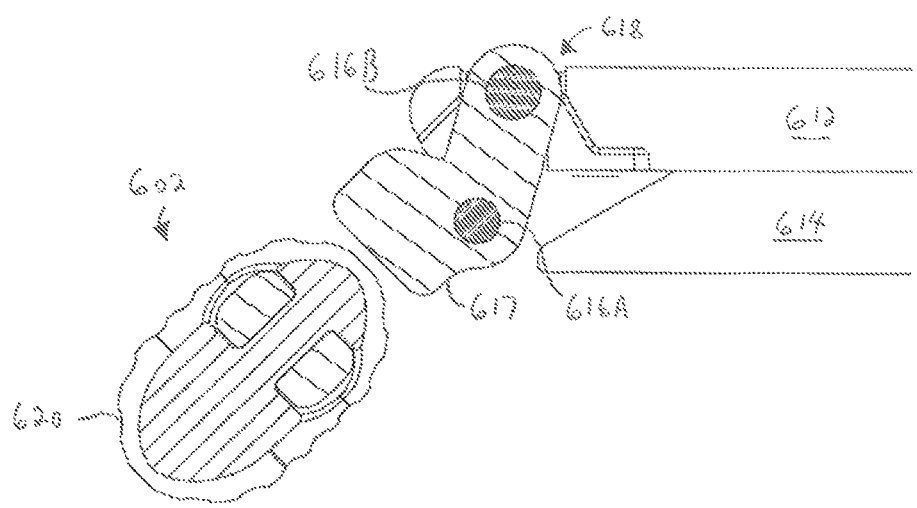
Figure 7C:
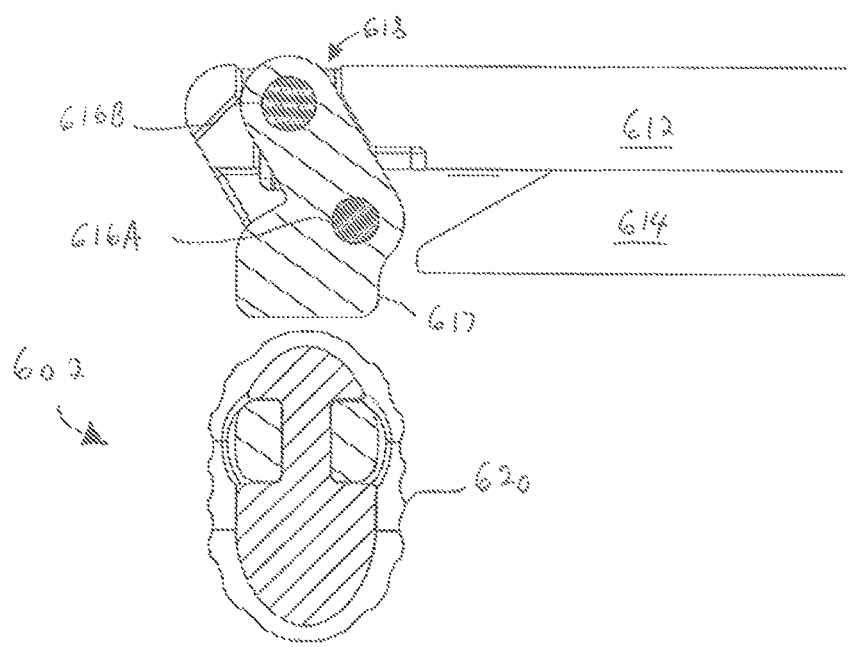
Figure 8A:
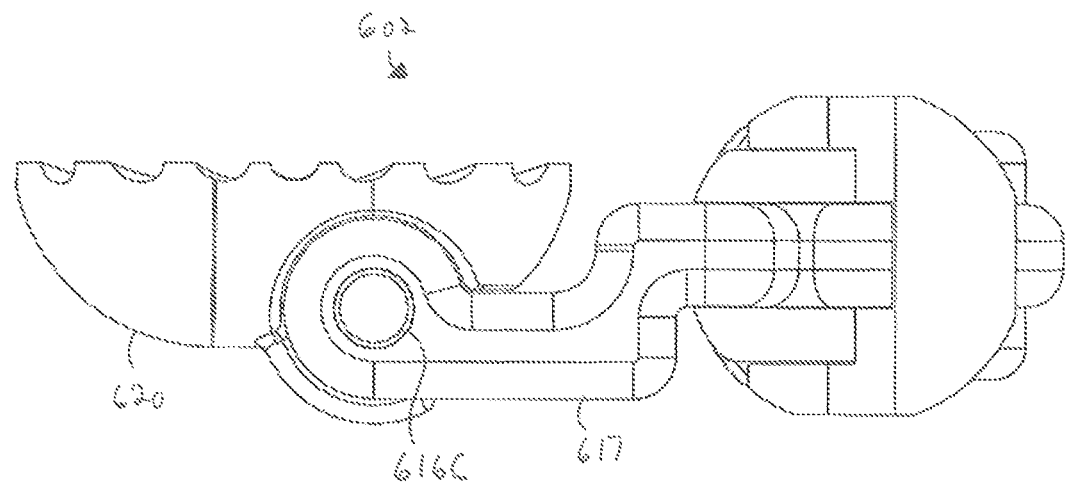
FIGS. 8A-8B depict close-up views of an articulating end effector of a discectomy tool in accordance with embodiments of the present disclosure.
Figure 8B:
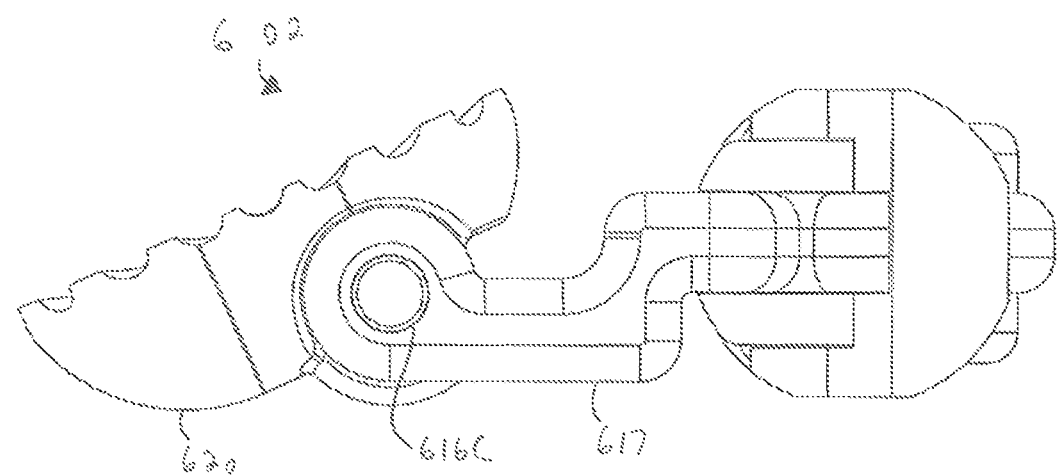

Referring now to FIGS. 6A-8B, an end effector 602 of surgical tool 600 in accordance with some embodiments of the present disclosure will be described. As depicted in these figures, the end effector of the tool 600 may be a cup curette. Because the tool 600 is substantially similar to the tool 100 described above, only a distal portion of the tool 600 is depicted in these figures and described below. FIGS. 6A and 7A depict the distal end of the tool 600 in an initial position (i.e., insertion position) and FIGS. 6B and 7C depict the distal end of the tool 600 in a final position (i.e., fully extended position). FIG. 7B depicts the distal end of the tool 600 in an intermediate position.

The tool 600 is configured to be inserted into the disc space in the initial position (FIGS. 6A and 7A), and then articulated once inside. The articulation is controlled using a handle similar to the handle 106 discussed above. The articulation of the end effector 602 functions as an active pivot based on a two pin mechanism. A first pivot pin 616A is fixed to the end effector 602 and a lower arm 614 of the tool. A second pivot pin 616B is fixed only to the end effector 602, thus allowing the second pivot pin 616B to translate within an upper arm 612 of the tool 600. As the handle is actuated, the upper arm 612 translates forward (i.e., distally) relative to the lower arm 614. Because the second pivot pin 616B is not fixed to the upper arm 612, but instead allowed to translate, the end effector 602 begins to rotate about the first pivot pin 616A. The actuation continues until the upper arm 612 reaches a physical stop. The physical stop can either be accomplished by a slot 618 into which the second pivot pin 616B extends, or by some limitation on the handle used to actuate the tool 600.

In some embodiments, the end effector 602 also includes passive articulation (depicted in FIGS. 8A and 8B), which is realized when the end effector 602 (i.e., the cup curette head) contacts an endplate adjacent to the disc space. Once contact occurs, the end effector 602 will remain aligned with the endplate as long as pressure is maintained. The entire tool 600 can then be pulled back and forth, as a standard cup curette, to remove tissue from the endplates. To achieve such passive articulation, the end effector 602 includes a third pivot point 616C coupling a head 620 of the end effector 602 to a pivot arm 617. The end effector 602 is allowed to pivot about the third pivot point 616C.

The inventor has discovered that the active pivot of the tool 600 is advantageous because it does not suffer from the drawbacks associated with a tool having two fixed pivot pins, one that is translated and the other that is rotated about. The translating pin in such a device is always at a constant distance from the rotation pin, thus creating a radius. The passive pivot of the tool 600 advantageously accommodates the different endplate shapes of different patients. In contrast, a standard cup curette suffers from point loading, which can result in over-stress at a specific area of bone, potentially breaking through the endplate.

Figure 9A:
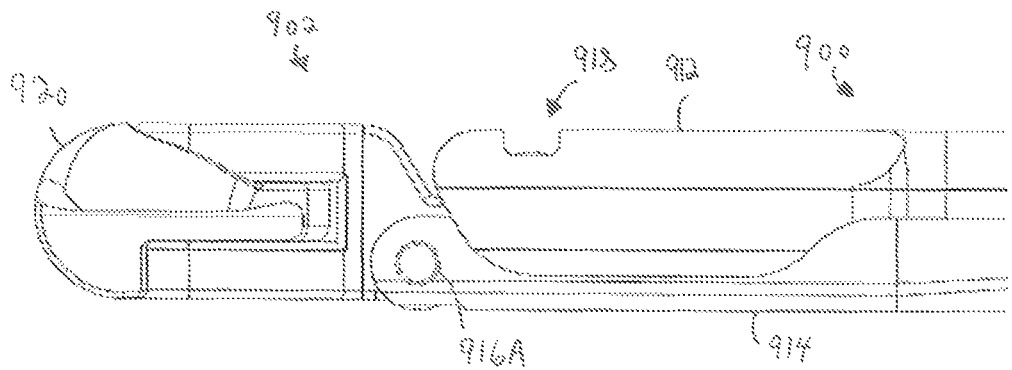
FIGS. 9A-9B depict an articulating end effector of a discectomy tool in accordance with embodiments of the present disclosure.
Figure 9B:
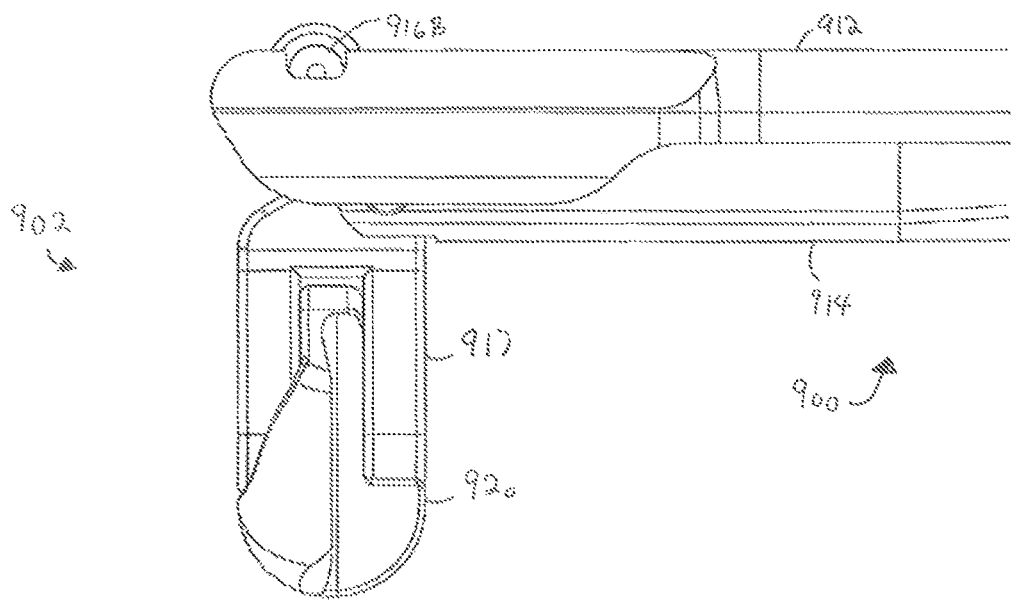
Figure 10A:
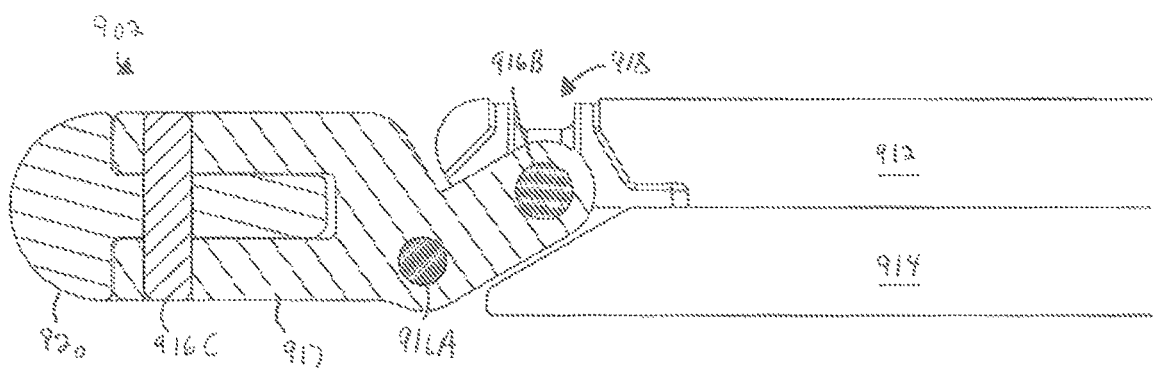
FIGS. 10A-10C depict cross-sectional views of the articulating end effector of a discectomy tool in accordance with embodiments of the present disclosure.
Figure 10B:
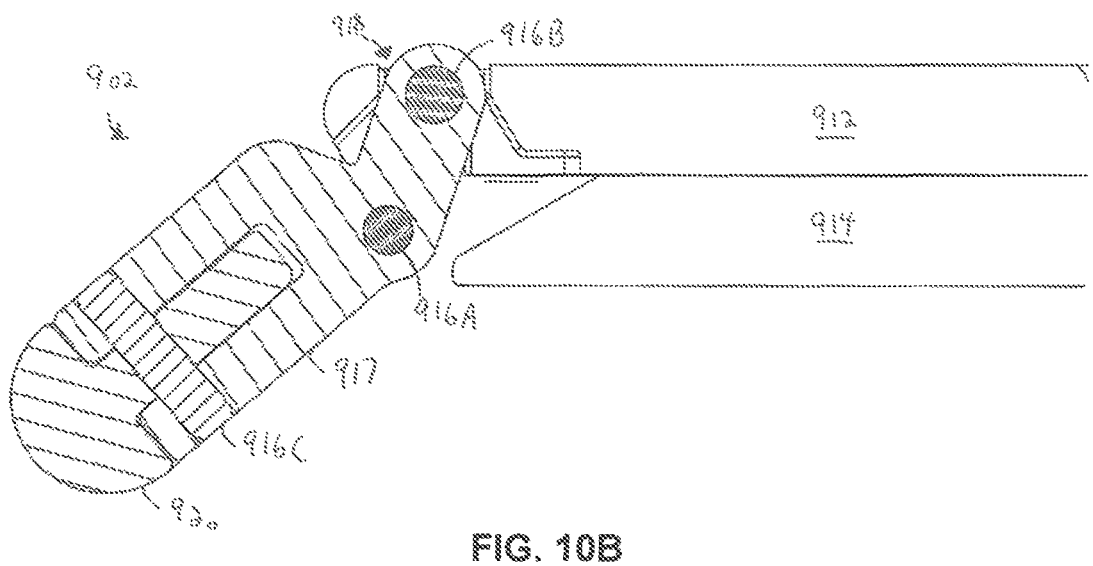
Figure 10C:
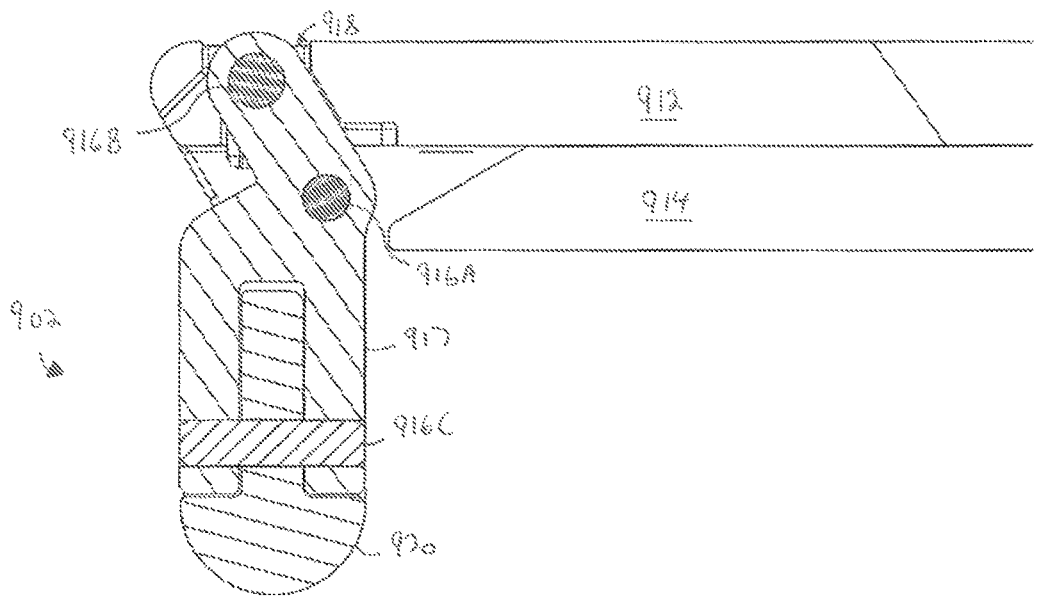

Referring now to FIGS. 9A-11C, an end effector 902 of surgical tool 900 in accordance with some embodiments of the present disclosure will be described. As depicted in these figures, the end effector of the tool 900 may be a rake. Because the tool 900 is substantially similar to the tool 100 described above, only a distal portion of the tool 900 is depicted in these figures and described below. FIGS. 9A and 10A depict the distal end of the tool 900 in an initial position (i.e., insertion position) and FIGS. 9B and 10C depict the distal end of the tool 900 in a final position (i.e., fully extended position). FIG. 10B depicts the distal end of the tool 900 in an intermediate position.

Similar to the tool 600, the tool 900 is configured to be inserted into the disc space in the initial position (FIGS. 9A and 10A), and then articulated once inside. The articulation is controlled using a handle similar to the handle 106 discussed above. The articulation of the end effector 902 functions as an active pivot based on a two pin mechanism similar to the one discussed above with respect to the tool 600. A first pivot pin 916A is fixed to the end effector 902 and a lower arm 914 of the tool. A second pivot pin 916B is fixed only to the end effector 902, thus allowing the second pivot pin 916B to translate within an upper arm 912 of the tool 900. As the handle is actuated, the upper arm 912 translates forward (i.e., distally) relative to the lower arm 914. Because the second pivot pin 916B is not fixed to the upper arm 912, but instead allowed to translate, the end effector 902 begins to rotate about the first pivot pin 916A. The actuation continues until the upper arm 912 reaches a physical stop. The physical stop can either be accomplished by a slot 918 into which the second pivot pin 916B extends, or by some limitation on the handle used to actuate the tool 900.

Figure 11A:
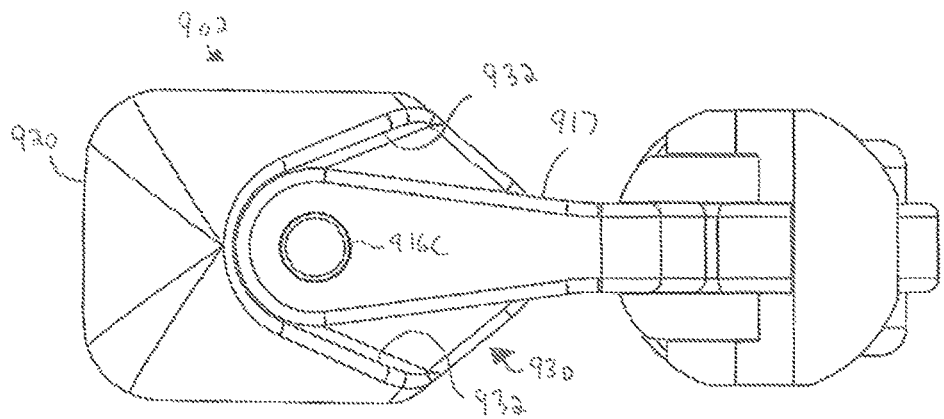
FIGS. 11A-11C depict close-up views of an articulating end effector of a discectomy tool in accordance with embodiments of the present disclosure.
Figure 11B:
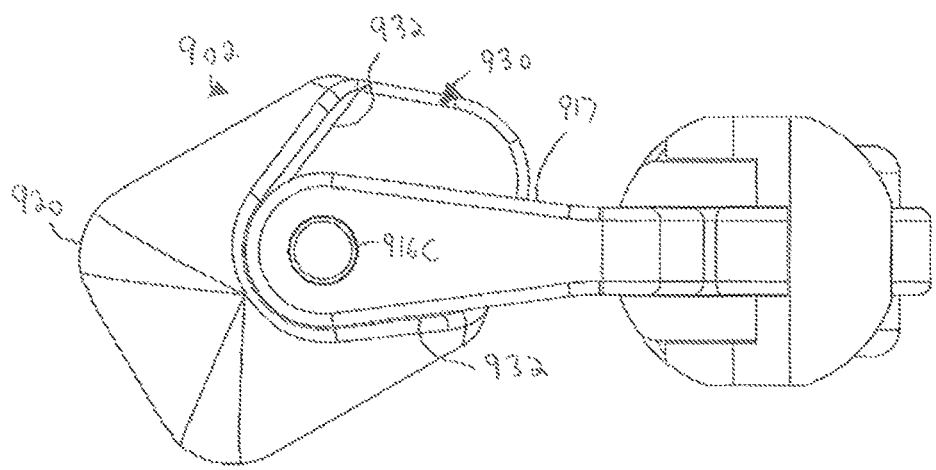
Figure 11C:
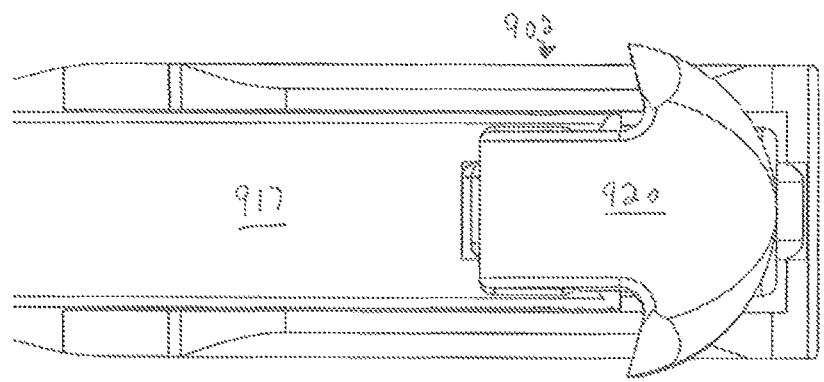

In some embodiments, the end effector 902 also includes passive articulation (depicted in FIGS. 11A and 11B), which is realized when the end effector 902 (i.e., the rake head) contacts an endplate adjacent to the disc space. Once contact occurs, the end effector 902 will remain aligned with the endplate as long as pressure is maintained. The entire tool 900 can then be pulled back and forth, as a standard cup curette, to remove tissue from the endplates. To achieve such passive articulation, the end effector 902 includes a third pivot point 916C coupling a head 920 of the end effector 902 to a pivot arm 917. The end effector 902 is allowed to pivot about the third pivot pin 916C. As shown in FIGS. 11A and 11B, the head of the end effector 902 may include an opening 930 surrounding the third pivot pin 916C to allow the head 920 to pivot about the third pivot pin 916C. As shown in FIG. 11B, the opening 930 may include walls 932 to limit such pivoting by abutting against the pivot arm 917. FIG. 11C depicts a top view of the head 920 of the end effector 902 (i.e., the rake head).

Figure 12A:
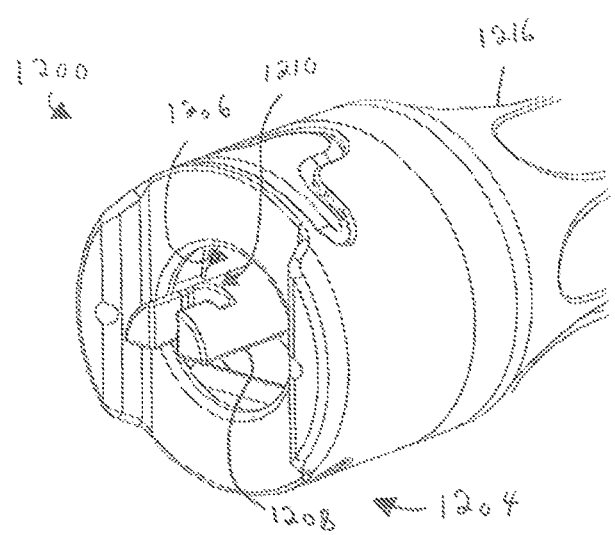
FIGS. 12A-12D depict a removable handle for use with a discectomy tool in accordance with embodiments of the present disclosure.
Figure 12B:
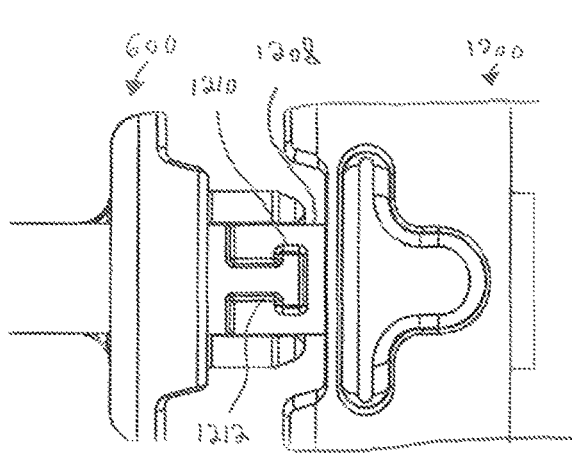
Figure 12C:
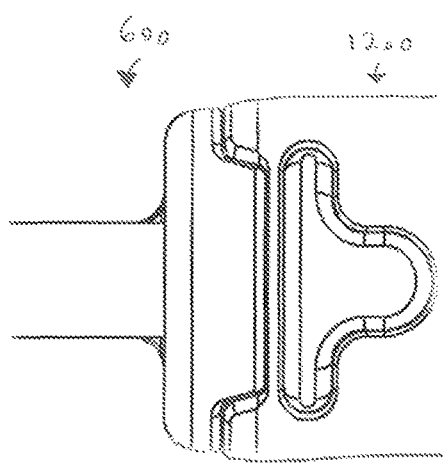
Figure 12D:
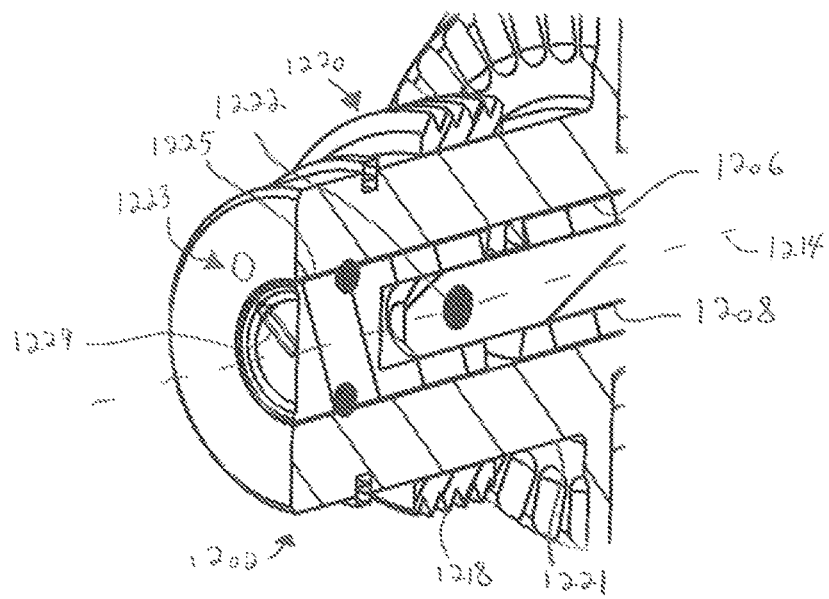

Referring to FIGS. 12A-14C, a handle 1200 for use with a surgical tool (e.g., tool 600) in accordance with embodiments of the present disclosure will be described. Although reference is made to the tool 600 in the following description of the handle 1200, it should be noted that any surgical tool requiring actuation (e.g., tools 100, 900) may be utilized with the handle 1200. The handle 1200 may be a modular handle that can be attached to multiple tools such as, for example, the tools described above. Such a handle replaces conventional handles such as handle 106 discussed above. In some embodiments, the handle 1200 extends from a proximal end 1202 to a distal end 1204 and includes a central channel 1206 extending from a distal end 1204 to a point between the proximal and distal ends 1202, 1204. The handle 1200 further includes an attachment arm 1208 disposed within the central channel 1206 and configured to mate with a corresponding feature of a tool to which the handle 1200 is attached. In some embodiments, the attachment arm 1208 includes a feature 1210 configured to receive a corresponding feature 1212 of the tool to which the handle 1200 is attached. In some embodiments, the feature 1210 may be a t-shaped slot, as shown in FIGS. 12A-12C. However, the feature 1210 may alternatively have any geometry capable of attaching the handle 1200 to the tool. The attachment arm 1208 is moveable along an axis 1214 of the handle 1200. As such, whichever portion of the tool the attachment arm 1208 is coupled to is also moved back and forth with the movement of the attachment arm 1208. In some embodiments, the attachment arm is coupled to a portion of the tool that needs to be moved in order for an end effector (e.g., 602) of the tool to articulate (e.g., one of the upper or lower arms 612, 614).

In some embodiments, the handle 1200 includes a knob 1216 having internal threads (not shown) that correspond to external threads 1218 of a carrier 1220. The carrier 1220 surrounds a body 1221 of the handle 1200 and is coupled to the attachment arm 1208 via a pin 1222. As such, when the knob 1216 is rotated, the threads cause the carrier 1220 to move back and forth along the body 1221, which in turn also causes the attachment arm 1208 to move back and forth, thus also moving the portion of the tool to which the attachment arm 1208 is attached.

Figure 13A:
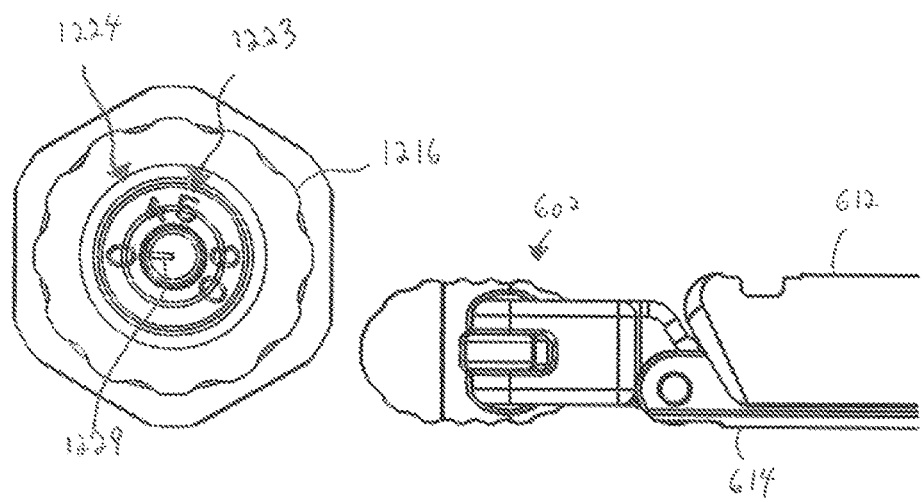
FIGS. 13A-13C depict an indicator disposed on the removable handle of FIGS. 12A-12D in accordance with embodiments of the present disclosure.
Figure 13B:
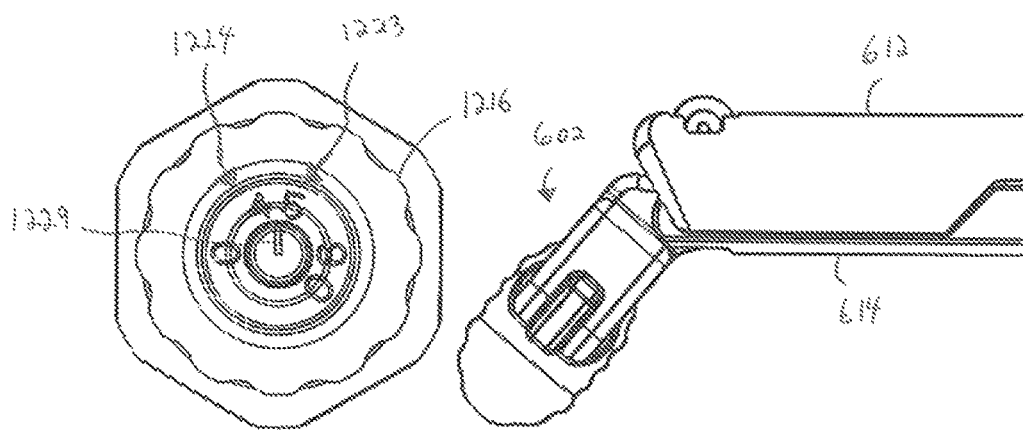
Figure 13C:
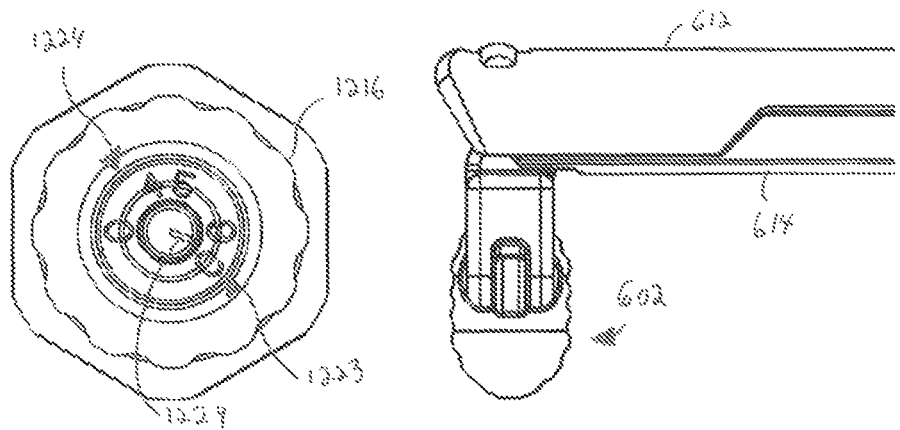
Figure 14A:
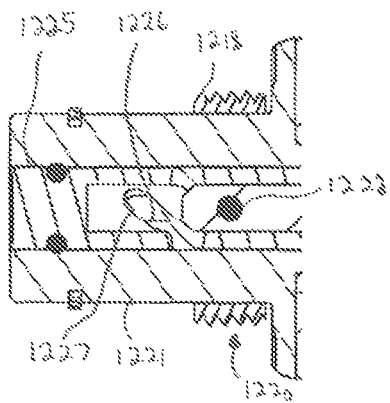
FIGS. 14A-14C depicts cross-sectional views of the removable handle of FIGS. 12A-12D at different positions of the articulating portion.
Figure 14B:
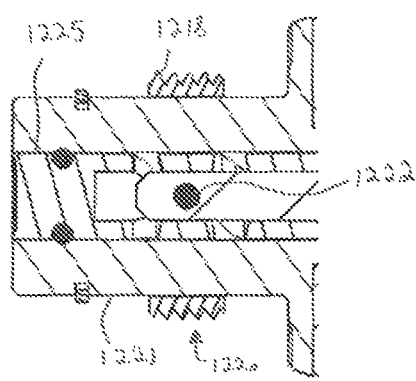
Figure 14C:
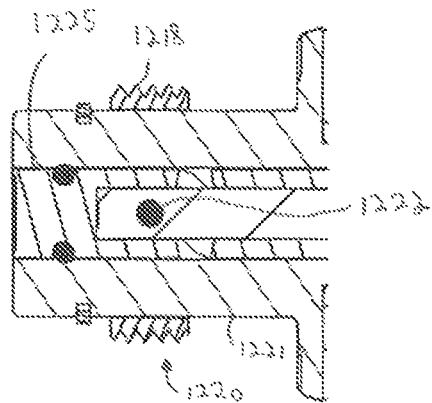
Figure 15:
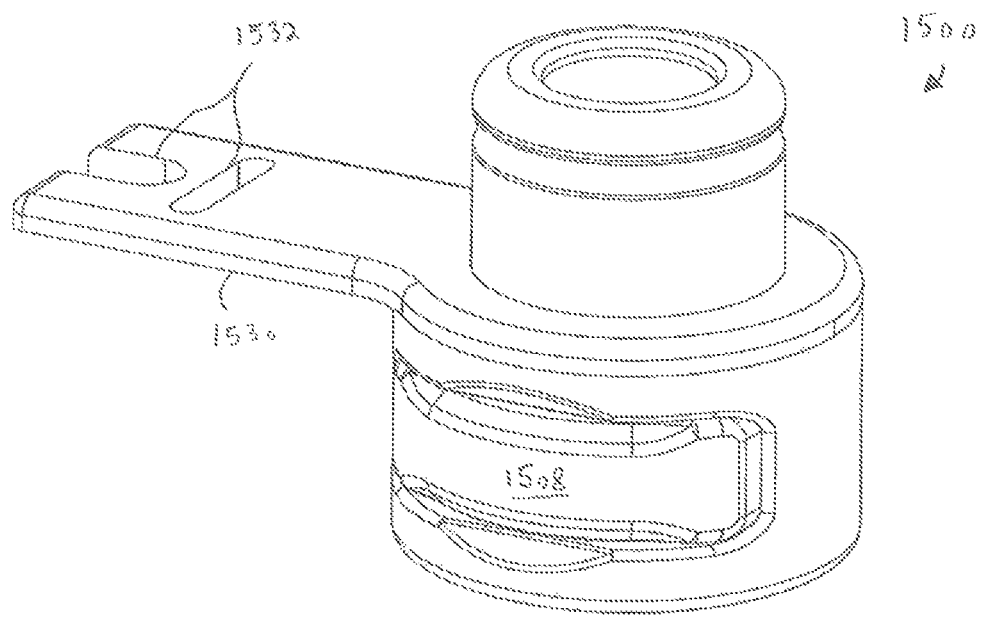
FIG. 15 depicts an isometric view of an adjustable stop in accordance with embodiments of the present disclosure.
Figure 16A:
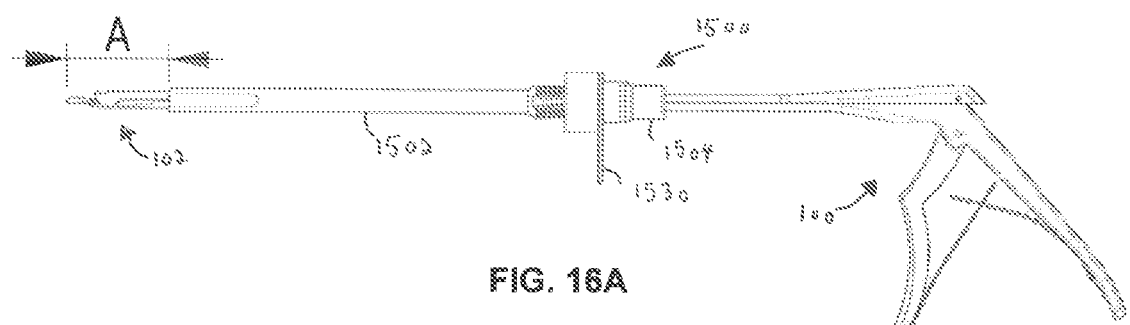
FIGS. 16A-16B depict the adjustable stop of FIG. 15 coupled to a discectomy tool in accordance with embodiments of the present disclosure.
Figure 16B:
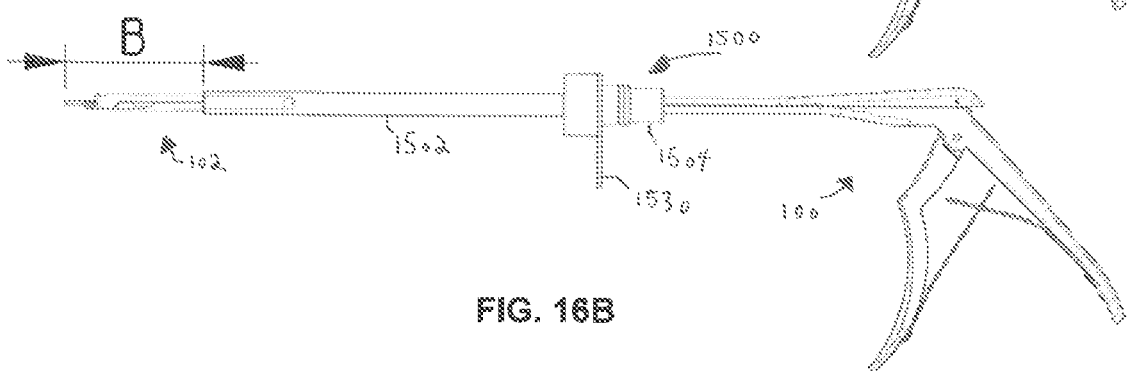
Figure 17A:
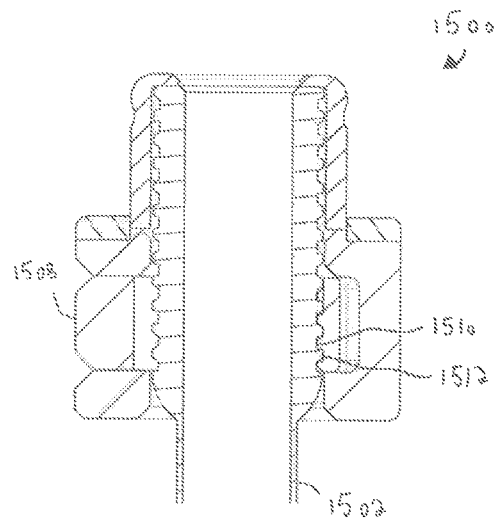
FIGS. 17A-17B depict cross-sectional views of the adjustable stop of FIG. 15.
Figure 17B:
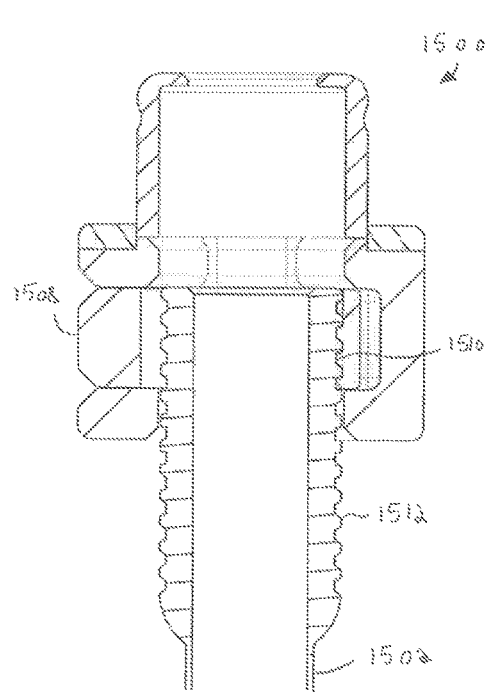
Figure 18A:
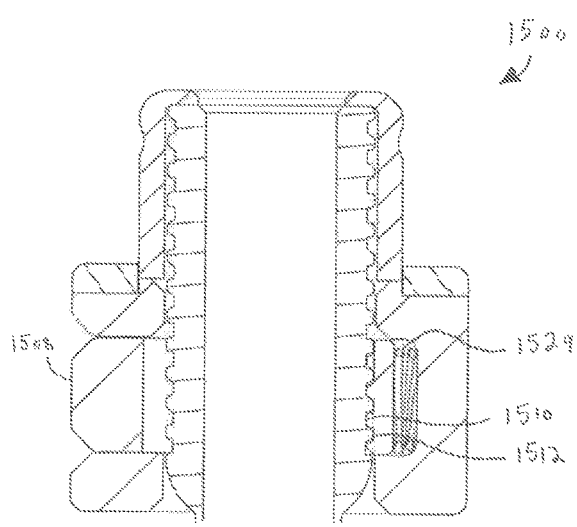
FIGS. 18A-18B depict cross-sectional views of the adjustable stop of FIG. 15.
Figure 18B:
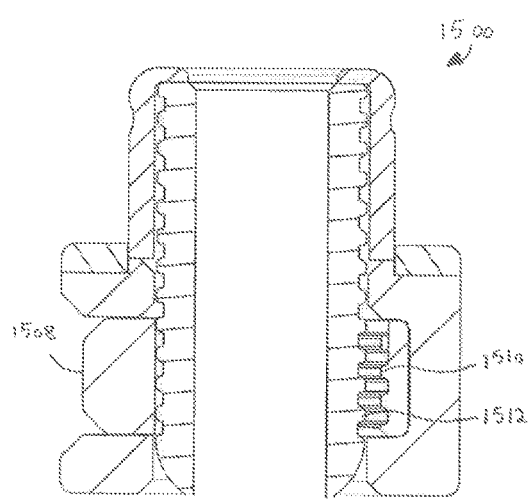

As depicted in FIGS. 13A-13C, in some embodiments, the handle 1200 may include an indicator 1224 configured to indicate the angular position of the end effector relative to the tool. In some embodiments, the indicator 1224 includes numerical values 1223 written on a proximal surface of the body 1221 and a pointer 1229 on a proximal surface of an indicator body 1225. In such an embodiment, the pin 1222 passes through a linear slot 1226 (FIG. 14A) formed in the body 1221 and a helical slot 1227 formed in the indicator body 1225 (similar to the adjustable stop 500 discussed above). As a result, rotation of the knob 1216 causes the linear movement of the carrier 1220, which causes the pin 1222 to move along the linear slot 1226 and the helical slot 1227 as shown in FIGS. 14A-14C. The movement of the pin along the helical slot 1227 causes the indicator body 1225 to rotate, thus also rotating the pointer 1229 causing it to point to the correct numerical value 1223 corresponding to the angular position of the end effector 602, as depicted in FIGS. 13A-13C.

Referring to FIGS. 15-18B, an adjustable stop 1500 for use with a surgical tool (e.g., tool 100) to limit the amount of travel of the end effector (e.g., end effector 102) of the tool into the disc space in accordance with embodiments of the present disclosure will be described. Although reference is made to the tool 100 in the following description of the adjustable stop 1500, it should be noted that any surgical tool requiring an adjustable stop (e.g., tools 600, 900) may be utilized with the adjustable stop 1500. The adjustable stop 1500 is coupled to a cannula 1502 through which the tool is inserted into the disc space. Each tool includes a hard stop 1504 (e.g., a collar or shoulder) that typically limits the amount of travel of the tool through the cannula 1502. The adjustable stop 1500 is moved to a desired position along the cannula 1502 such that when the hard stop 1504 contacts the adjustable stop 1500, the tool cannot be advanced further into the cannula 1502. As a result, the distance traveled by the end effector of the tool beyond a distal end 1506 of the cannula 1502 is limited to a desired distance. FIGS. 16A and 17B depict the adjustable stop 1500 positioned at the highest position along a proximal portion of the cannula 1502. The tool protrudes beyond the distal end 1506 of the cannula 1502 a distance A at this stop position. FIGS. 16B and 17A depict the adjustable stop 1500 position at the lowest position along the proximal portion of the cannula 1502. The tool protrudes beyond the distal end 1506 of the cannula a distance B, which is greater than the distance A, at this stop position.

In some embodiments, the position of the adjustable stop 1500 is adjustable using interacting features on the proximal portion of the cannula 1502. In such an embodiment, the adjustable stop 1500 includes a moveable body 1508 that includes a first set of teeth 1510 that mate with a second set of teeth 1512 on the cannula 1502. When the first and second sets of teeth 1510, 1512 are engaged (FIG. 18A), the adjustable stop 1500 is prevented from moving along the cannula 1502. When the teeth are disengaged (FIG. 18B), the position of the adjustable stop 1500 may be adjusted. To engage and disengage the teeth, the moveable body 1508 is pressed/moved such that the first set of teeth 1510 are moved out of engagement with the second set of teeth 1512. The adjustable stop 1500 further includes a spring element 1529 configured to bias the moveable body 1508 towards the engaged position (i.e., the position in which the first and second sets of teeth 1510, 1512 are engaged).

In some embodiments, the adjustable stop 1500 further includes a table mount 1530 configured to mount the adjustable stop 1500 to a table. In some embodiments, the table mount 1530 extends outwardly from one side of the adjustable stop 1500 and may include one or more openings 1532 configured to receive fixation elements (not shown) to fix the position of the adjustable stop 1500 (and anything coupled to it) with respect to the table.

When performing an extraforaminal disc prep, surgeons need to navigate an initial trajectory through Kambin's triangle. This can be performing using any suitable instrument (e.g., a spinal needle, a JamShidi®, a k-wire, etc.). Kambin's triangle has one leg defined by the exiting nerve root of the surgical level. If care is not taken during the initial stab, damage to this nerve can occur. The inventor has developed a k-wire that can address this need.

Figure 19:
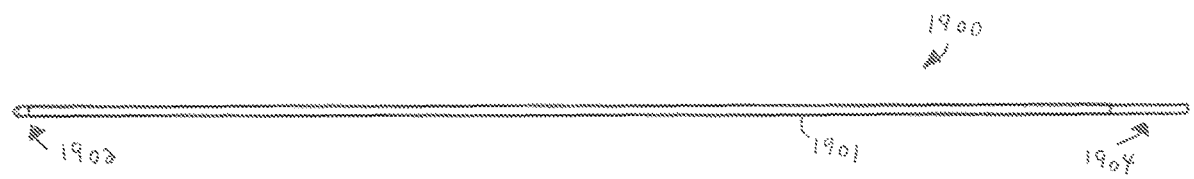
FIG. 19 depicts a k-wire in accordance with embodiments of the present disclosure.

FIG. 19 depicts a k-wire 1900 in accordance with embodiments of the present disclosure. At least a portion of the k-wire 1900 has a coating 1901 formed of a polymer such as Halar®. In some embodiments, about 2-3 mm of a first end 1902 of the k-wire 1900 is exposed and about 20-30 mm of a second end 1904 are exposed. The k-wire 1900 has a stainless steel core, which is conductive and can, therefore, be used with a neuro-monitoring system. A lead (not shown) can be attached to the second end and stimulated. The coating 1901 allows the k-wire to be insulated from the patient's anatomy surrounding the k-wire 1900, thus focusing the stimulation around the nerve (i.e., at the first end 1902). As a result, an initial trajectory can be neuromonitored or stimulated in a manner in which only the area of interest (i.e., the exiting nerve root) is stimulated.

All references cited herein are expressly incorporated by reference in their entirety. There are many different features to the present invention and it is contemplated that these features may be used together or separately. Unless mention was made above to the contrary, it should be noted that all of the accompanying drawings are not to scale. Thus, the invention should not be limited to any particular combination of features or to a particular application of the invention. Further, it should be understood that variations and modifications within the spirit and scope of the invention might occur to those skilled in the art to which the invention pertains. Accordingly, all expedient modifications readily attainable by one versed in the art from the disclosure set forth herein that are within the scope and spirit of the present invention are to be included as further embodiments of the present invention.

What is claimed is:

1. An articulating rake for use in removing tissue from a patient, comprising:
    a handle;
    an elongate first arm coupled to the handle and defining a first longitudinal axis;
    an elongate second arm coupled to the handle and defining a second longitudinal axis parallel to the first longitudinal axis;
    first and second pivot pins;
    a pivot arm coupled to the second arm via the first pivot pin and having a proximal portion translationally coupled to the first arm;
    a translation pin attached to the proximal portion of the pivot arm and only slidably coupled to a slot in the first arm so as to allow a translational movement of the translation pin lateral to the first longitudinal axis and within the first arm; and
    an end effector pivotably coupled to the pivot arm via the second pivot pin defining a pivoting axis transverse to the first pivot pin,
    wherein actuation of the handle longitudinally translates the second arm relative to the first arm to cause the pivot arm to rotate about the first pivot pin while the proximal portion of the pivot arm translates laterally relative to the first longitudinal axis,
    wherein the actuation continues until the first arm reaches a physical stop by abutting against the pivot arm.

2. The articulating rake of claim 1, wherein the end effector is sized to be inserted into a vertebral disc space through a cannula.

3. The articulating rake of claim 1, wherein the articulating rake is sized and dimensioned for laparoscopy.

4. The articulating rake of claim 1, wherein the handle includes a trigger, and wherein squeezing of the trigger causes articulation of the end effector about the first pivot pin.

5. The articulating rake of claim 1, wherein the handle is a modular handle that extends from a proximal end to a distal end and comprises:
    a body having a central channel extending from the distal end to a point between the proximal end and the distal end;
    a carrier disposed around the body and having external threads;
    a knob surrounding the body and the carrier, the knob having internal threads corresponding to the external threads of the carrier, wherein rotation of the knob causes linear translation of the carrier along an axis of the handle;
    an attachment arm disposed within the central channel and coupled to the carrier via a pin, wherein the attachment arm is configured to mate with a corresponding feature of the articulating rake.

6. The articulating rake of claim 5, wherein the modular handle includes an indicator configured to indicate an angular position of the end effector with respect to a rest of the articulating rake.

7. The articulating rake of claim 1, further comprising:
    an adjustable stop configured to be coupled to a cannula through which the articulating rake is configured to be inserted into an intervertebral disc space, wherein a position of the adjustable stop along the cannula is adjustable to limit a distance by which the end effector extends beyond a distal end of the cannula, wherein the adjustable stop includes a first set of teeth selectively engageable with a second set of teeth on the cannula to lock and unlock translation of the adjustable stop along the cannula.

8. The articulating rake of claim 7, wherein the adjustable stop further includes a table mount configured to allow the adjustable stop to be mounted to a table.

9. The articulating rake of claim 1, wherein the end effector is one of a ring curette, a rake, or a cup curette.

10. The articulating rake of claim 1, wherein the end effector is a ring curette, and wherein a sweep angle of the ring curette is about 160°.

11. An articulating rake for use in removing tissue from a patient, comprising:
    A modular handle extending from a proximal end to a distal end, the handle including:
        a body having a central channel extending from the distal end to a point between the proximal end and the distal end;
        a carrier disposed around the body and having external threads;
        a knob surrounding the body and the carrier, the knob having internal threads corresponding to the external threads of the carrier, wherein rotation of the knob causes linear translation of the carrier along an axis of the handle; and
        an attachment arm disposed within the central channel and coupled to the carrier;
    an elongate first arm coupled to the handle and defining a first longitudinal axis;
    an elongate second arm disposed along the first arm, the second arm coupled to the handle and defining a second longitudinal axis parallel to the first longitudinal axis;
    first and second pivot pins;
    a pivot arm coupled to the second arm via the first pivot pin and having a proximal portion translationally coupled to the first arm;
    a translation pin attached to the proximal portion of the pivot arm and only slidably coupled to a slot in the first arm so as to allow a translational movement of the translation pin lateral to the first longitudinal axis and within the first arm; and
    an end effector pivotably coupled to the pivot arm via the second pivot pin defining a passive articulation mechanism and a pivoting axis transverse to the first pivot pin,
    wherein actuation of the handle longitudinally translates the second arm relative to the first arm to cause the pivot arm to rotate about the first pivot pin while the proximal portion of the pivot arm translates laterally relative to the first longitudinal axis,
    wherein the actuation continues until the first arm reaches a physical stop by abutting against the pivot arm.

12. The articulating rake of claim 11, wherein the articulating rake is configured to be inserted into a vertebral disc space through a cannula.

13. The articulating rake of claim 11, wherein the articulating rake is sized and dimensioned for laparoscopy.

14. The articulating rake of claim 13, wherein the modular handle includes an indicator configured to indicate an angular position of the end effector with respect to a rest of the articulating rake.

15. The articulating rake of claim 11, further comprising:
   an adjustable stop configured to be coupled to a cannula through which the articulating rake is configured to be inserted into an intervertebral disc space, wherein a position of the adjustable stop along the cannula can be adjusted to limit a distance by which the end effector extends beyond a distal end of the cannula, wherein the adjustable stop includes a first set of teeth selectively engageable with a second set of teeth on the cannula to lock and unlock translation of the adjustable stop along the cannula.

16. The articulating rake of claim 15, wherein the adjustable stop further includes a table mount configured to allow the adjustable stop to be mounted to a table.

17. The articulating rake of claim 11, wherein the end effector is one of a ring curette, a rake, or a cup curette.

18. The articulating rake of claim 11, wherein the end effector is a ring curette, and wherein a sweep angle of the ring curette is about 160°.

\* \* \* \* \*